United States Patent
Lattanzi

(10) Patent No.: US 6,866,623 B2
(45) Date of Patent: Mar. 15, 2005

(54) CENTRIFUGE HAVING A MAGNETIC ACTUATOR FOR LOADING AND UNLOADING BUCKETS AND A METHOD OF LOADING/UNLOADING THE BUCKETS ON THE CENTRIFUGE

(75) Inventor: Giuseppe Lattanzi, Cinisello Balsamo (IT)

(73) Assignee: Jouan Italia S.r.l., Milan (IT)

( * ) Notice: Subject to any disclaimer, the term of this patent is extended or adjusted under 35 U.S.C. 154(b) by 143 days.

(21) Appl. No.: 10/286,772

(22) Filed: Nov. 4, 2002

(65) Prior Publication Data

US 2004/0087426 A1 May 6, 2004

(51) Int. Cl.[7] .............................................. B04B 5/02
(52) U.S. Cl. ......................................... 494/20; 220/230
(58) Field of Search ................................ 494/1, 16, 20, 494/21, 37, 85; 220/230; 422/72, 102

(56) References Cited

U.S. PATENT DOCUMENTS

| | | | | |
|---|---|---|---|---|
| 4,110,552 A | * | 8/1978 | Lombardi | 220/230 |
| 4,927,545 A | * | 5/1990 | Roginski | 210/360.1 |
| 5,322,497 A | | 6/1994 | Kobayashi | |
| 5,730,697 A | | 3/1998 | Auchinleck | |
| 6,196,961 B1 | * | 3/2001 | Hoshiba et al. | 494/20 |
| 6,383,126 B1 | * | 5/2002 | Fondin | 494/10 |
| 6,758,803 B2 | * | 7/2004 | Jang | 494/10 |

FOREIGN PATENT DOCUMENTS

| | | |
|---|---|---|
| DE | 2210648 | 9/1973 |
| DE | 3425922 A1 | 1/1986 |
| EP | 0753747 A2 | 7/1997 |
| EP | 1270078 A1 * | 1/2004 |
| JP | 1-167055 * | 6/1989 |
| JP | 9-85130 * | 3/1997 |

* cited by examiner

Primary Examiner—Charles E. Cooley
(74) Attorney, Agent, or Firm—Nixon & Vanderhye, P.C.; Frank P. Presta

(57) ABSTRACT

For automated centrifugation of samples contained in test tubes, a centrifuge (c) has a rotating head (11) with swing-out buckets (30) for housing the test tubes. Apparatus is provided for automatically positioning each bucket in the centrifugation chamber under a safety lid and to lift each bucket out of the centrifugation chamber. Magnetic devices are provided to retain a cover on its bucket and a magnetic system is provided for removing the cover of each bucket in order to expose the test cubes to a robotic arm or similar device.

12 Claims, 7 Drawing Sheets

CENTRIFUGE HAVING A MAGNETIC ACTUATOR FOR LOADING AND UNLOADING BUCKETS AND A METHOD OF LOADING/UNLOADING THE BUCKETS ON THE CENTRIFUGE

BACKGROUND OF THE INVENTION

1. Field of the Invention

A commonly used type of centrifuge for laboratories comprises a rotor or rotating head carrying swing buckets pivotally carried on respective axes transverse to the rotation axis of the rotor. The swing buckets have housings, each for receiving a test tube containing a sample or specimen to be centrifuged. During operation, the rotor rotates around its axis (generally vertical) and each swing bucket swings about its axis (generally horizontal) toward an horizontal or nearly horizontal position, and the content thereof is subject to centrifugal force.

Automated centrifuging systems are being used in laboratories for the treatment of biological samples, solutions and suspensions, contained into test tubes, bottles and/or microtiter plates. In these areas automated centrifuges are required with the following features: they must be controllable by an external computer system; the door or a smaller opening thereof must be opened and closed automatically to allow for bucket removal; the motor and its controller must be able to bring each of the buckets to the handling position and hold it therein; imbalance tolerance should be higher than for standard centrifuges. The present invention relates to an apparatus and a method apt to be integrated into an automated analysis, control and process for biological, chemical, pharmacological, toxicological, alimentary, environmental research and correlated activities.

2. Description of the Related Art

Apparatus for automating the centrifugation step in an automatic biological or related analysis system have been disclosed by various inventors.

CA 2,232,932 discloses a swing bucket centrifuge assembly wherein the centrifuge buckets are open-sided for permitting the loading-unloading of test tubes by means of a robot-type loading/unloading mechanism, when a bucket is in a loading-unloading position above the centrifuge top platform. The centrifuge disclosed in the Canadian patent is not suitable for operating with buckets having a bucket cover.

Other inventors do not disclose how to take the cover away from the swing out buckets, or leave this task to the robotic arm or other device of the combined test suite; thus increasing complication and workload of the devices.

The present invention is aimed at solving the above problem.

SUMMARY OF THE INVENTION

More particularly, an aim of the invention is to allow automated operation in tests involving a centrifugation, including automated loading/unloading of buckets and automated applying/removing of bucket covers, in a relatively uncomplicated way.

Another aim is to achieve the above in a cost-effective way.

The invention foresees a bucket-handling apparatus in a centrifuge particularly but not exclusively for biological tests, and a method, wherein a bucket for tube tests is retained in position and/or the cover thereof is removed by handling means comprising magnetic engaging means. A bucket assembly is also provided, which has a base and a cover and magnetic means for retaining the cover on the base.

The invention reaches the above aims, in particular it allows an automated functioning, it is able to remove/apply bucket covers, it is efficient and cost-effective.

BRIEF DESCRIPTION OF THE DRAWINGS

The present invention will be more clearly understood by reference to the schematic drawings together with the detailed description that follows. The drawings show an unrestrictive exemplary embodiment of the invention, wherein.

DESCRIPTION OF THE PREFERRED EMBODIMENTS

Figure 1:
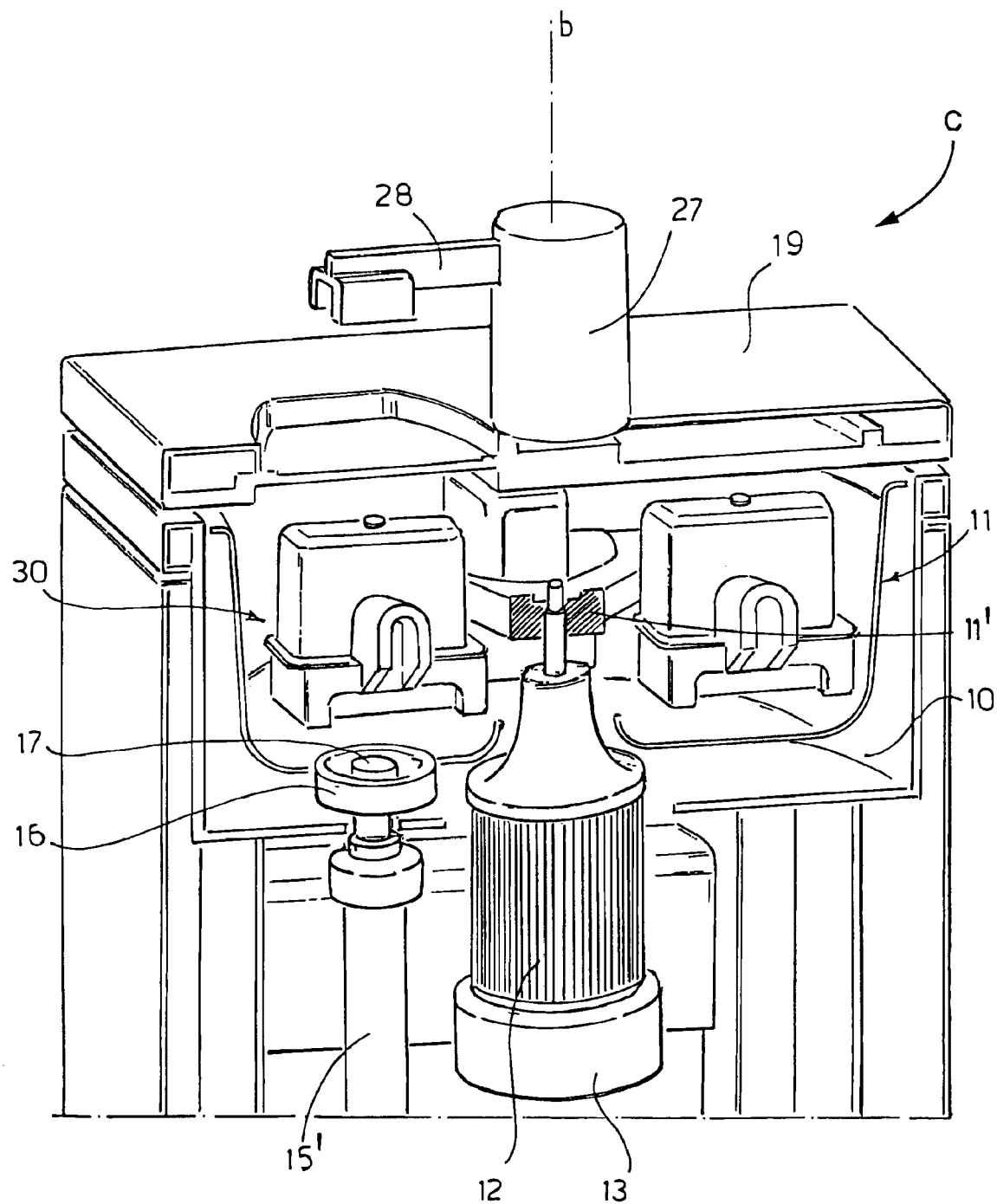
FIG. 1 is an axonometric part-sectional view of a centrifuge for test tubes according to the invention, in a condition with the buckets retracted within the rotating head.

In FIG. 1 a centrifuge C is disclosed to which an apparatus of the invention is applied. A rotating head 11 in a centrifuging chamber 10 of the centrifuge comprises a per-se known spider element 11' defining (by pivots e.g.) transversal pivotal axes a for swing-out buckets, said buckets 30 having seats for accommodating a plurality of test tubes. The rotating head is driven by an asynchronous electric motor 12. The angular position of the motor shaft and accordingly of the rotating head is read by using an angular encoder 13 fitted to the motor shaft beneath the motor body, as it is shown in FIG. 2, although other means to accomplish the same result are possible within the scope of the present invention.

Power is supplied to motor 12 under control of an electronic system 14, which comprises a microprocessor managing the electrical waveform with a twofold purpose: that is, to control the rotational speed of the rotating head to satisfy the requirements for the centrifugation process; and to control its stopping position to allow handling of the test tubes of each individual bucket. The microprocessor is also coded to control other functions, which will be disclosed presently. The present invention is not concerned with the programmation and implementation details of the software, which might be conceived in a variety of ways, all compatible with the scope of the invention.

Figure 2:
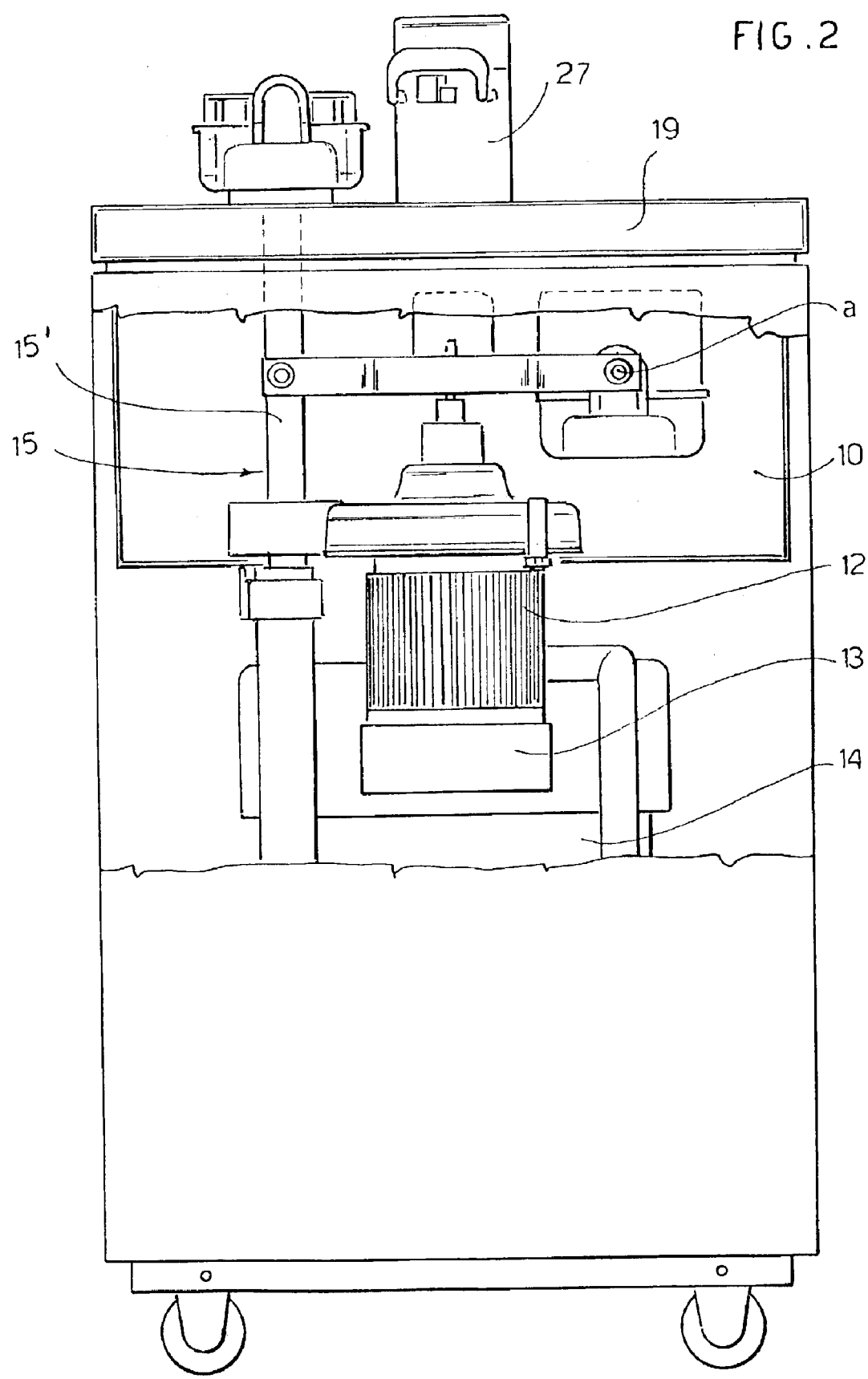
FIG. 2 is a part-sectional elevational view of the centrifuge of FIG. 1, wherein the centrifuge is shown with a bucket extended over the centrifuge safety cover.
Figure 3:
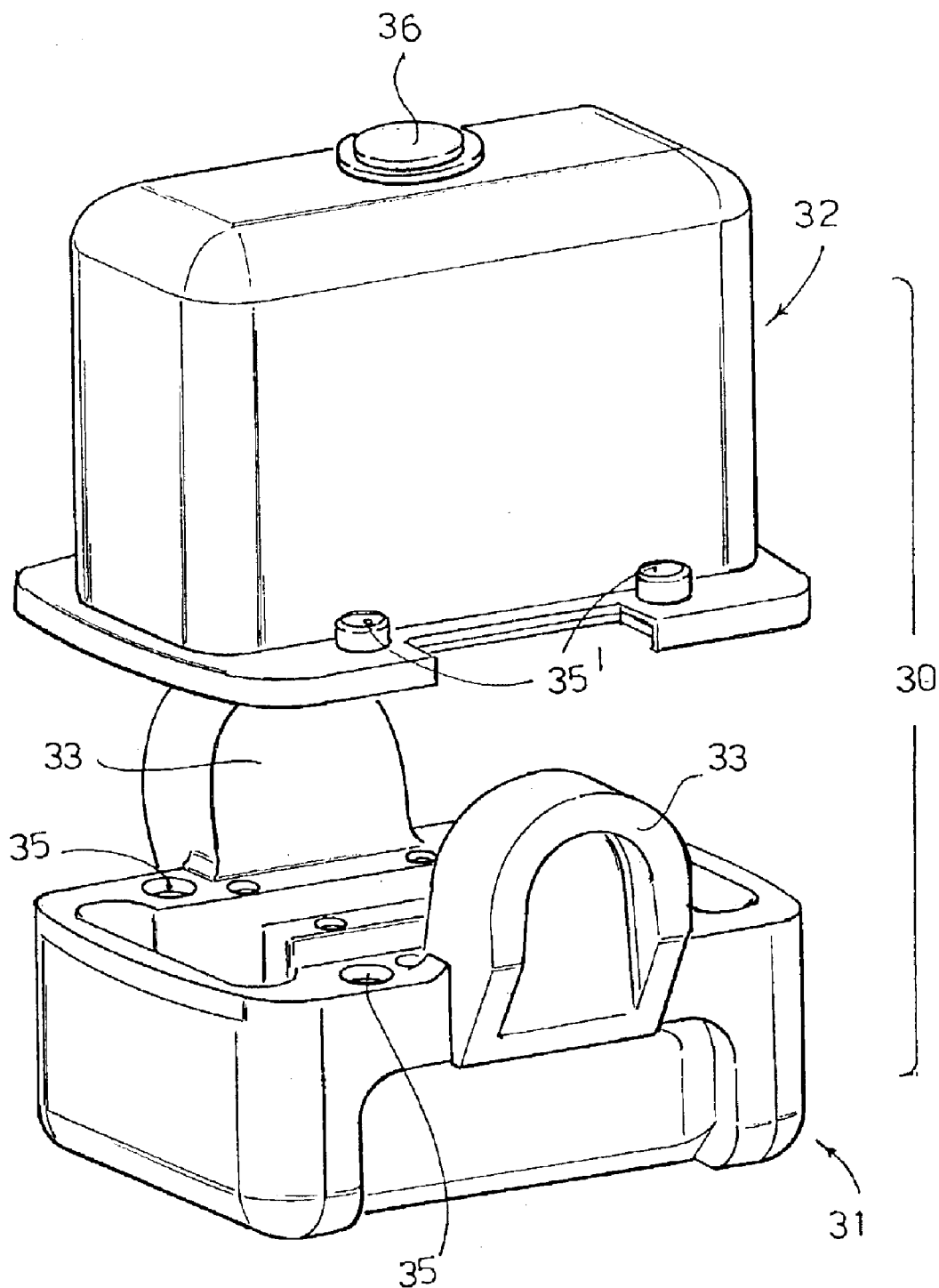
FIG. 3 is an axonometric exploded view, enlarged with respect to the previous figures, of a bucket with the bucket cover raised with respect to the bucket base.

A vertical actuator 15 for loading/unloading the buckets is shown in FIGS. 1, 2, 3 and in the present embodiment of the invention is of a type comprising a vertical actuator rod 15' with a screw driven by an electric motor through a reducing gear train (not shown), and with a built-in potentiometer for position feedback. Both drive and feedback element could be of a different construction.

Figure 2A:
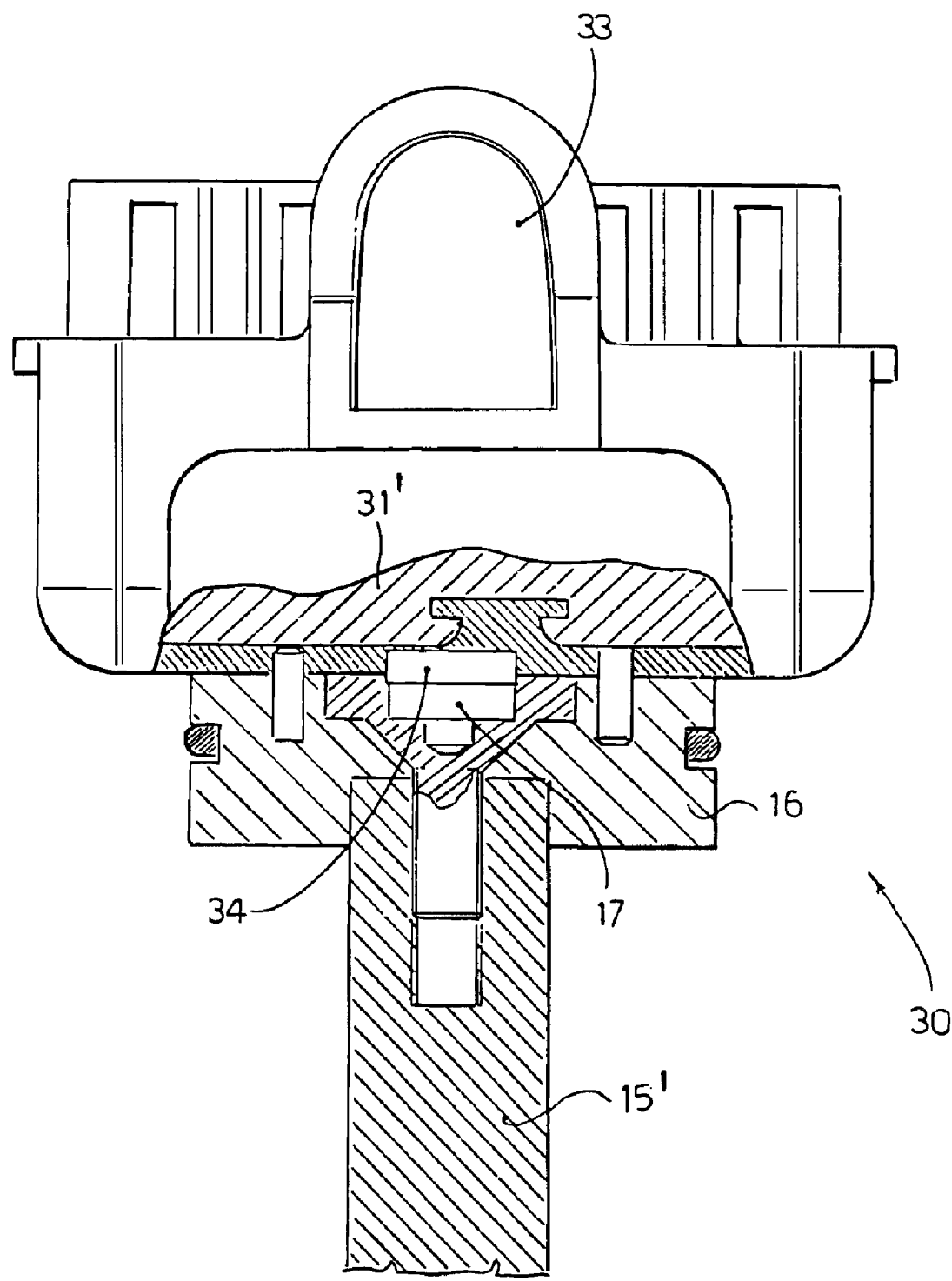
FIG. 2A shows the encircled detail of FIG. 2 in an enlarged scale.

At its upper end the actuator rod 15' (FIG. 2A) has a bucket support plate 16, which is provided in its center with a recess accommodating a permanent magnet 17.

A bucket of the invention is shown in FIG. 3 and referenced 30 as a whole. The bucket comprises a base 31 and a cover 32. The base 31 in a per-se known way has an upwardly open housing for receiving a tube carrying body 31'—FIG. 2A—and test tubes (not shown). The base 31 has opposed mounting axis a pivots trunnions 33, 33 for pivotally mounting on the rotating head. According to a feature of the invention, the base has in its undersurface at least an operational magnet, referenced 34 (FIG. 2A), said magnet being for cooperating with the abovementioned magnet 17 of the support plate, so that when the bucket rests over the support plate the magnetic fields of the two magnets act to keep the bucket firmly against the support plate. The bucket base of the invention further has cover-retaining magnets 35, 35 on an upper surface thereof.

The bucket cover 32 has a downwardly open box-like shape, and is fitted with a small insert of magnetically soft steel 36, which is applied on its upper surface in a central position, such that when the bucket is at rest in the centrifuge chamber, the insert is on a same vertical line as the midpoint of the segment joining the end faces of the trunnions of the rotating head. The bucket cover further has a number of small cover-retaining magnets 35' symmetrically disposed on its undersurface, for cooperating with the cover-retaining magnets 35 of the base to retain the cover on the base.

The actuator 15 has an upward-downward stroke. The actuator stroke is long enough for allowing that at the lowest position of the actuator, the support plate has its upper surface at a lower vertical level than the undersurface of the bucket base, leaving the bucket hang freely from the rotating head; while at its highest position the support plate has the bucket resting thereon and secured thereto by the magnets out and above the centrifugation chamber and in a position required for handling the test tubes contained therein.

Figure 4:
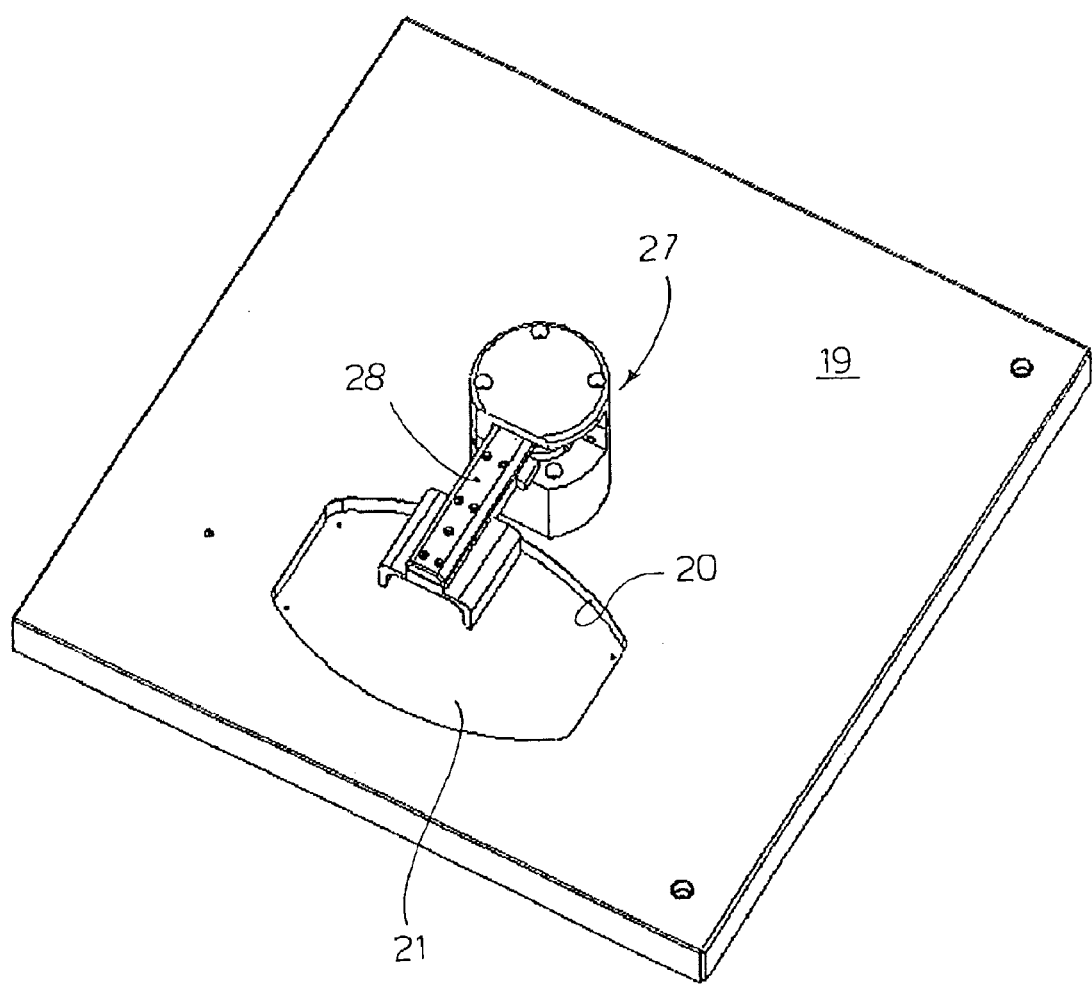
FIG. 4 is an axonometric view from above of a safety cover of the centrifuge and column with rotating arm.
Figure 5:
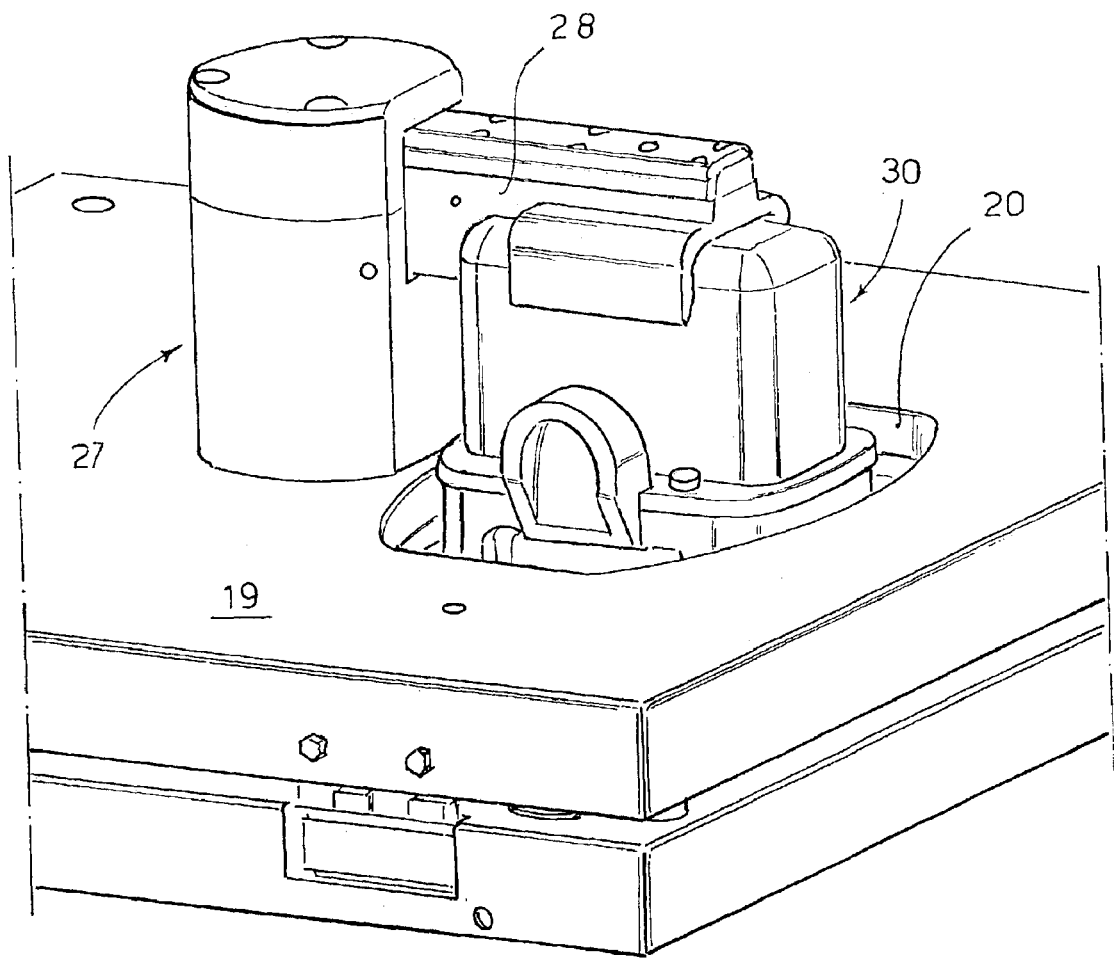
FIG. 5 is an enlarged perspective view of the column and rotating arm, engaging a bucket cover.
Figure 6:
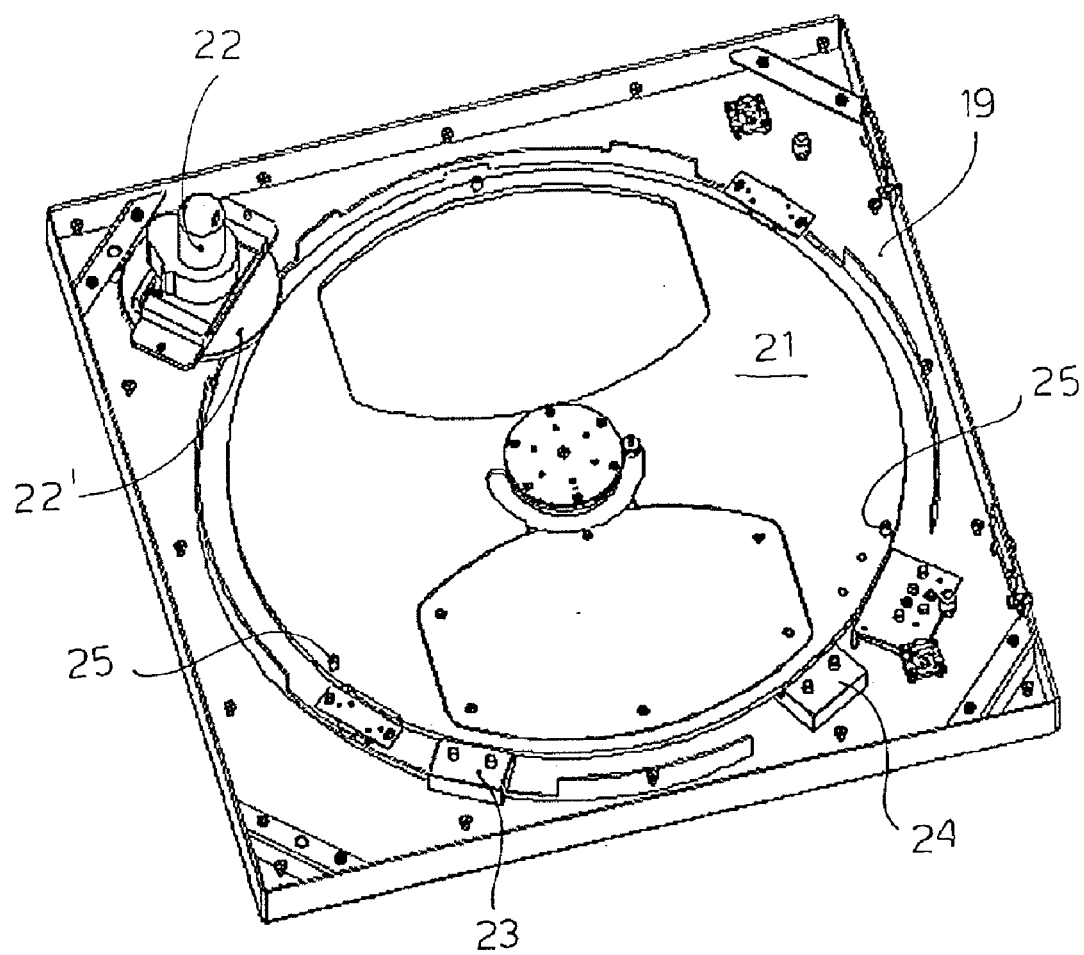
FIG. 6 is an axonometric view from below of the centrifuge safety cover with rotating lid.

A per-se known safety cover 19 of the centrifuge is shown in FIGS. 4 and 6. The cover can be opened manually for cleanup and maintenance purposes, while an opening 20 allows for bucket extraction. During centrifugation, a rotating lid 21 closes this opening; in the present embodiment of the invention a small electric motor 22 rotates the lid by means of a friction wheel 22', so this movement can in no way endanger the personnel working near the centrifuge; and the two extreme positions of the movement, corresponding to full opening and complete closure, are sensed and fed back to the microcontroller by means of two switches 23 and 24 operated by cam 25 in the lid; although a different system might be used in another embodiment of the invention.

FIGS. 1, 2, 4, 5 show a cover-handling device of the centrifuge. In the present embodiment of the invention it comprises a column 27 fitted on the upper surface of the safety cover 19; a rotating arm 28 pivoted at the top of column 27 and coaxial with the rotation axis of the centrifuge when the safety cover is closed. The rotation arm is able to rotate over an angular span as will be explained in the following.

The rotation is controlled by a microprocessor and in the present embodiment of the invention is accomplished by means of a small electric motor coupled to the rotating arm by a toothed belt, not shown in the drawing. rotating arm 28 is fitted with an electromagnet (not shown), whose magnetic field when its coil is energized acts downwards along a vertical axis which has the same distance from the rotation axis of the centrifuge as the distance between the rotation axis and the swinging axis of the swing out buckets.

A first condition for the angular rotation span of the rotating arm is that at one end of the rotation the action axis of the magnetic field of electromagnet of the arm points down to the midpoint of the segment joining the end faces of the two trunnions, over which the swing out bucket rests; it being understood that the segment is considered when the bucket is put at rest in correspondence with the opening of the safety cover. That this first condition can be accomplished at all derives from what has been said about the distance of the magnetic axis from the rotation axis b. A second condition for the angular rotation span of the rotating arm is that at the other end of the rotation the action axis of the magnetic field of the electromagnet points down to an area of the upper surface of the safety cover that is designated as the parking area of the bucket cover.

Other ways for removing the bucket cover from the bucket prior to its handling are within the scope of the present invention. For example the pivoting axis of the rotating arm could be in a different position with respect to the one described above; or else, the removal of the bucket cover can be made with a translational movement, the electromagnet being guided by rails or by a bar linkage; all these different solutions being embodiments of this invention, which foresees that the electromagnet points down to the bucket cover, gripped and then bringing it away to its designated parking location.

Couples of magnets 35, 35' keeps the cover firmly against the bucket base.

The working cycle of the automated centrifuge will now be described, starting from a condition in which the centrifuge is running at full speed. Following a signal from the management program, the electric drive decelerates; the rotation encoder and the control program bring the bucket to be handled to stop under the lid opening, which by now is still safely closed. When the microprocessor gets a confirmation that rotation is stopped, it issues a command to open the rotating safety lid 21. Then another command begins extension of the vertical actuator 15, which during centrifugation remained in its fully retracted position. In its upward movement the top plate of the actuator reaches the bottom of the bucket, and the permanent magnets 17 and 34 secure the bucket to the plate. After having taken hold of the bucket the actuator extends to full stroke.

The height of electromagnet of the rotating arm 28 is such, when the arm is fully extended, the steel insert 36 in the bucket cover makes a positive contact with the poles of the electromagnet of the rotating arm, with an interference being compensated by the compliance of the rotating arm 28. When the electromagnet of the rotating arm is energized its magnetic action upon the insert 36 is sufficient to overcome the weight of the bucket cover plus the mutual magnetic forces of the permanent magnets 35 and 35', that keep the bucket cover over the bucket. When the electromagnet is not energized the residual magnetic field in it and in the steel insert 36 is not sufficient to overcome these forces.

When actuator 15 is fully extended as detected by its feedback potentiometer the microprocessor issues a command to energise the electromagnet of the rotating arm, and after that the actuator is retracted for a length, causing the bucket cover to separate from the bucket base while remaining attached to the electromagnet of the arm, as a consequence of what has been said about the attractive force between electromagnet and insert 36.

Then the rotating arm pivots bringing the bucket cover to its parking area, after the bucket 30 has been lowered by the actuator 15 by a length sufficient for the cover to clear the bucket lugs 33 and the top of the test tubes during its movement. This is the cited condition determining the retraction span.

Thereafter, the actuator extends again to bring the bucket 30 at a level appropriate for handling of the test tubes therein contained by the robotic arm of the automated analysis system. When handling is completed, the described movements and actions are performed in reverse order until the bucket fitted with its cover rests with its lugs 33 upon the trunnions or pivots of the rotating head inside the centrifugation chamber.

What is claimed is:

1. A centrifuge for buckets comprising a rotating head (11) rotatable around a rotation axis (b) in a centrifugation chamber (10) of the centrifuge, head trunnions integral with the rotating head and defining swing axes (a) for the buckets, a safety cover (19), an actuator for loading the buckets on the respective trunnions of the rotating head and unloading the buckets therefrom, characterised in that said actuator (15) has magnetic bucket engaging means (17) for retaining a bucket (30) thereon.

2. A centrifuge as said in claim 1, further comprising bucket handling means (27, 28) for handling a bucket outside the centrifugation chamber, characterised in that said bucket handling means comprise magnetic means for engaging a bucket cover (32) provided with cooperating magnetic means (36) for cooperating with magnetic means of the handling means.

3. A centrifuge as said in claim 2, wherein said bucket handling means comprise a rotating column (27) coaxial with the rotation axis of the rotating head and a bucket handling arm (28) provided with said magnetic means.

4. A centrifuge as said in claim 2, for use with buckets provided with a bucket cover retained on a bucket base by magnetic means, characterised in that the magnetic means of the bucket handling means operate with a force that is stronger that the magnetic force retaining a bucket cover (32) on the bucket base (31).

5. A bucket for receiving sample test tubes for centrifuging in a centrifuge, said bucket comprising a base (31) and a removable cover (32), and having lugs (33) extending laterally outwardly from said base for swing mounting on trunnions of a centrifuge rotating head, characterised in that it further comprises magnetic means (35, 35') on said base and said cover for securing mutual engagement thereof, said magnetic means (35, 35') being of sufficient strength to retain said cover on said base during the rotation thereof in a centrifuge.

6. A bucket as said in claim 5 further comprising magnetic retaining means (34) in the base undersurface and/or magnetic retaining means (36) in the upper surface of the cover for cooperating with adjacent portions of a centrifuge when the bucket is disposed therein.

7. A bucket loading/unloading apparatus for a centrifuge for centrifuging buckets swingably applied on a centrifuge rotating head, characterised in that it comprises a vertical actuator (15) provided with a bucket-engaging plate (16) having magnetic means, said actuator being movable between a retracted position, wherein it is at a distance below a bucket supported on a centrifuge rotating head, and an extended position, wherein it presents a bucket to handling means outside of the centrifugation chamber.

8. A method for loading/unloading buckets on a rotating head (10) of a centrifuge, said buckets comprising a base (31) and a cover (32) having mutually engaging magnetic means and further magnetic means (34, 36) in the base undersurface and on the cover, said method comprising the following steps a. applying a bucket on a loading/unloading actuator (15) of the centrifuge b. retaining the bucket thereon by means of magnetic force c. retracting the actuator and leaving the bucket applied onto the rotating head (10).

9. A method for loading/unloading buckets on a rotating head (10) of a centrifuge, said buckets comprising a base (31) and a cover (32) having mutually engaging magnetic means and further magnetic means (34, 36) in the base undersurface and on the cover, said method comprising the following steps engaging a centrifuged bucket with loading/unloading actuator (15)

moving the actuator with the bucket thereon to an extended condition, wherein the bucket (30) is outside of the centrifugation chamber of the centrifuge magnetically engaging the bucket cover (32) with a movement arm (28) and applying thereto a magnetic force stronger than the magnetic force retaining the bucket cover on the bucket base, removing the bucket cover from the bucket base and transferring same to a parking area.

10. A method according to claim 9 wherein said transfer is a rectilineal movement.

11. A method according to claim 9 wherein said transfer is a rotational movement.

12. A method according to claim 9 characterized in that after applying a magnetic force to the cover, the actuator is retracted with the base over it, in order to leave free the movement of the arm 28 with the cover.

* * * * *